United States Patent [19]

Martindale

[11] Patent Number: 4,885,420
[45] Date of Patent: Dec. 5, 1989

[54] PROCESS FOR THE PRODUCTION OF AROMATIC HYDROCARBONS FROM OLEFINIC HYDROCARBONS

[75] Inventor: David C. Martindale, Roselle, Ill.

[73] Assignee: UOP, Des Plaines, Ill.

[21] Appl. No.: 265,376

[22] Filed: Oct. 31, 1988

[51] Int. Cl.$^4$ .......................... C07C 2/52; C07C 12/02
[52] U.S. Cl. .................................... 585/322; 585/415; 585/417
[58] Field of Search .................... 585/322, 415, 417

[56] References Cited

U.S. PATENT DOCUMENTS 3,827,968  8/1974  Givens et al. .................... 208/49
4,554,393  11/1985  Liberts et al. .................... 585/322
4,686,312  8/1987  Chu et al. .................... 585/315

FOREIGN PATENT DOCUMENTS 0162636  11/1985  European Pat. Off. .

*Primary Examiner*—Curtis R. Davis
*Attorney, Agent, or Firm*—Thomas K. McBride; John F. Spears, Jr.

[57] ABSTRACT

Disclosed is a multi-stage catalytic process for the production of aromatics from a feedstock comprising $C_2$–$C_5$ olefins. The process comprises the steps of: (1) passing a hydrocarbon feedstock comprising $C_2$–$C_5$ olefins into a hydrogenation reaction zone in the presence of a hydrogen and a hydrogenation catalyst to produce a hydrogenation reaction zone product essentially free of olefins; and (2) passing the hydrogenation reaction zone product into a dehydrocyclodimerization reaction zone containing a dehydrocyclodimerization catalyst at conditions whereby a dehydrocyclodimerization reaction zone product comprising aromatics is produced.

13 Claims, 1 Drawing Sheet

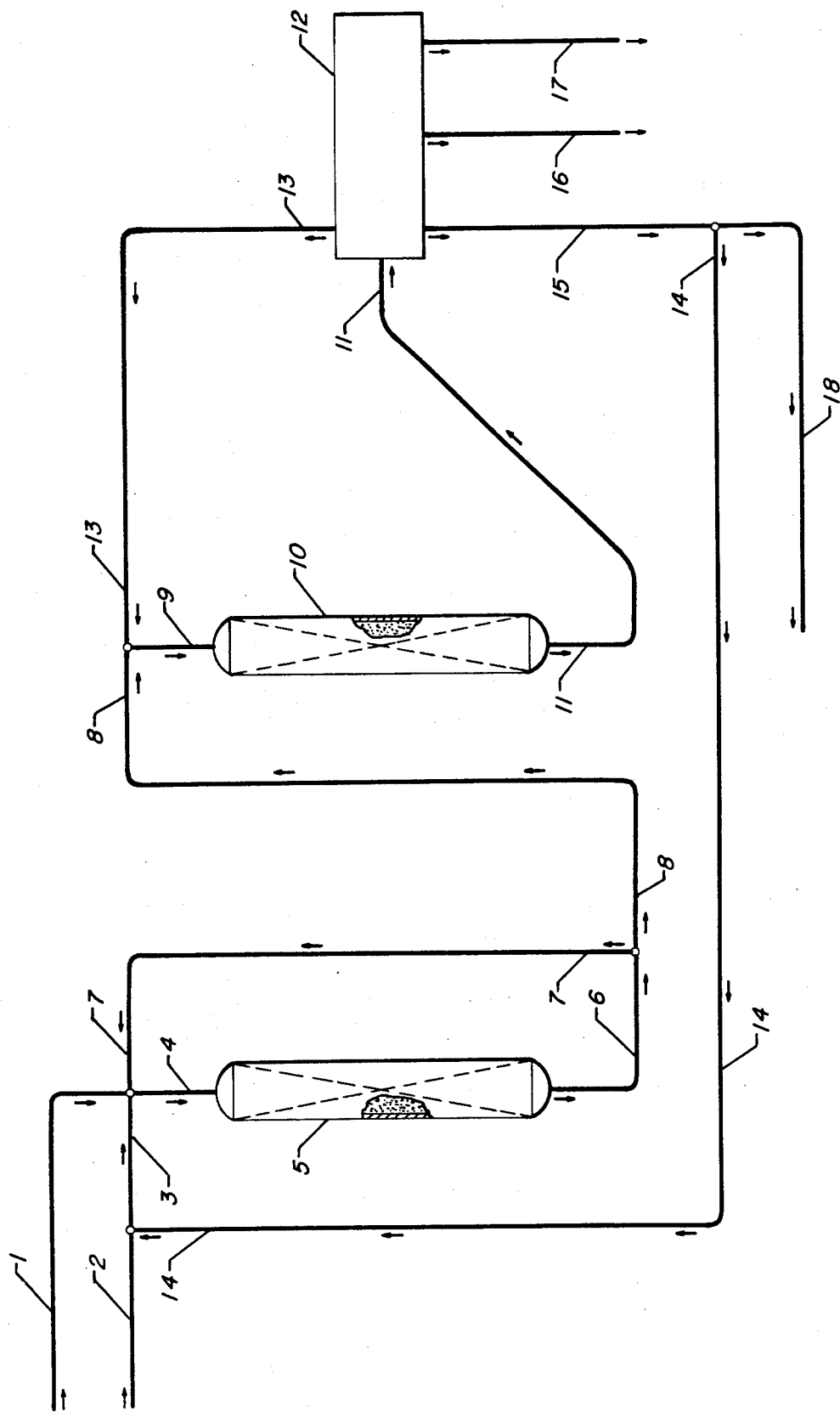

PROCESS FOR THE PRODUCTION OF AROMATIC HYDROCARBONS FROM OLEFINIC HYDROCARBONS

BACKGROUND OF THE INVENTION

The present invention relates to a two-stage process effective in converting $C_2$–$C_5$ olefinic hydrocarbons into aromatic hydrocarbons via hydrogenation and dehydrocyclodimerization, respectively.

Dehydrocyclodimerization is a reaction where reactants comprising paraffins and olefins, containing from 2 to 5 carbon atoms per molecule, are reacted over a catalyst to produce primarily aromatics with $H_2$ and light ends as by-products. This process is quite different from the more conventional reforming or dehydrocyclization process where $C_6$ and higher carbon number reactants, primarily paraffins and naphthenes, are converted to aromatics. These aromatics contain the same or less number of carbon atoms per molecule versus the reactants from which they are formed, indicating the absence of dimerization reactions. In contrast, the dehydrocyclodimerization reaction results in an aromatic product that always contains more carbon atoms per molecule than the $C_2$–$C_5$ reactants, thus indicating that the dimerizing reaction is a primary step in the dehydrocyclodimerization process. Typically, the dehydrocyclodimerization reaction is carried out at temperatures in excess of 260° C. using dual functional catalysts containing acidic and dehydrogenation components. These catalysts include acidic amorphous aluminas which contain metal promoters. Recently, crystalline aluminosilicates have been successfully employed as catalyst components for the dehydrocyclodimerization reaction. Crystalline aluminosilicates, generally referred to as zeolites, may be represented by the empirical formula:

$$M_{2/n} \cdot Al_2O_3 \cdot xSiO_2 \cdot yH_2O$$

in which n is the valence of M which is generally an element of Group I or II, in particular, sodium, potassium, magnesium, calcium, strontium, or barium and x is generally equal to or greater than 2. Zeolites have skeletal structures which are made up of three-dimensional networks of $SiO_4$ and $AlO_4$ tetrahedra, corner linked to each other by shared oxygen atoms. The greater the proportion of the $SiO_4$ species to the $AlO_4$ species, the better suited the zeolite is for use as a component in dehydrocyclodimerization catalysts. Such zeolites include mordenite and the ZSM variety. In addition to the zeolite component, certain metal promotes and inorganic oxide matrices have been included in dehydrocyclodimerization catalyst formulations. Examples of inorganic oxides include silica, alumina, and mixtures thereof. Metal promoters such as Group VIII or Group III metals of the Periodic Table have been used to provide the dehydrogenation functionality. The acidic function can be supplied by the inorganic oxide matrix, the zeolite, or both.

The use of olefins as a feedstock to a dehydrocyclodimerization reaction zone has been found to result in a lower aromatic selectivity and increased catalyst deactivation (coking) in comparison to a paraffinic feedstock. The rapid deactivation is believed to be caused by excessive carbon formation (coking) on the catalyst surface. This coking tendency makes it necessary to frequently perform costly and time-consuming catalyst regenerations. Reducing catalyst coking tendencies and thereby increasing catalyst life is a particular object to which this application is directed.

OBJECTS AND EMBODIMENTS

A principal object of this invention is to provide an improved process for the conversion of an olefinic hydrocarbon feedstock into an aromatic-containing hydrocarbon product. Further, this process results in a reduction in the catalyst deactivation rate and an improvement in the conversion selectivity of the dehydrocyclodimerization reaction zone catalyst in comparison to conventional single-step processes employing an olefin feed. Accordingly, a broad embodiment of the present process is directed towards a continuous multi-stage catalytic process for producing aromatic hydrocarbons from a feedstock comprising $C_2$–$C_5$ olefins. The process comprises the steps of passing the $C_2$–$C_5$ hydrocarbon feedstock comprising olefins along with hydrogen into a hydrogenation reaction zone containing a hydrogenation catalyst and operated at hydrogenation reaction conditions to produce a hydrogenation reaction zone product comprising 50 mole % fewer olefins than in $C_2$–$C_5$ feedstock. The hydrogenation reaction zone product is then passed into a dehydrocyclodimerization reaction zone containing a dehydrocyclodimerization catalyst and operated at dehydrocyclodimerization reaction conditions to produce a dehydrocyclodimerization reaction zone product comprising hydrogen, methane, ethane, ethylene, $C_3$–$C_5$ aliphatic hydrocarbons, and $C_6$+aliphatic and aromatic hydrocarbons. Finally, the dehydrocyclodimerization reaction zone product is separated into fractions comprising light gases such as hydrogen, methane, ethane and ethylene, a $C_3$–$C_5$ aliphatic hydrocarbon recycle stream and a $C_6$+aliphatic and aromatic hydrocarbon product stream. In a narrower embodiment, the continuous multi-stage catalytic process of this invention comprises the steps of passing a $C_2$–$C_5$ hydrocarbon feedstock comprising olefins along with hydrogen into a hydrogenation reaction zone containing a hydrogenation catalyst and operated at hydrogenation conditions including a temperature of from 50° to 150° C., a pressure of from 1.0 to 25 atmospheres, and a liquid hourly space velocity of from 0.1 to 20 $hr^{-1}$ to produce a hydrogenation reaction zone product comprising essentially no olefins. The hydrogenation reaction zone product comprising essentially no olefins is then passed into a dehydrocyclodimerization reaction zone along with recycled $C_2$–$C_5$ aliphatic hydrocarbons recovered in the separation zone. The dehydrocyclodimerization reaction zone contains a dehydrocyclodimerization catalyst and is operated at dehydrocyclodimerization reaction conditions including a temperature of form 400° to 650° C., a pressure of from 0.25 to 10 atmospheres, and a liquid hourly space velocity of from 0.5 to 10 $hr^{-1}$ to produce a dehydrocyclodimerization reaction zone product comprising hydrogen, methane, ethane, ethylene, $C_3$–$C_5$ aliphatic hydrocarbons, and $C_6$+aliphatic and aromatic hydrocarbons. Finally, the fractions are recovered and a fraction comprising $C_2$–$C_5$ aliphatic hydrocarbons is recycled to the inlet of the dehydrocyclodimerization reaction zone.

INFORMATION DISCLOSURE

The prior art recognizes a number of two-reaction stage processes for the production of aromatics from a hydrocarbon feedstock comprising $C_2$-$C_5$ olefinic hydrocarbons. Of these processes, none embodies all of the aspects of the two-reaction stage conversion process of the present invention nor is it apparent that these processes have the same benefits and advantages of the unique process of this invention.

U.S. Pat. No. 4,554,393 to Liberts et al discloses a process for the production of aromatics from a predominantly paraffinic feedstock by the steps of dehydrogenation followed by cyclodimerization of the alkenes in a second reactor. The process of this invention differs in at least one manner from that of the '393 disclosure in that the second reaction of the instant invention is dehydrocyclodimerization which dehydrogenates alkanes to alkenes and then cyclodimerizes the resulting dehydrogenated hydrocarbons. The second reaction of this invention performs both reaction steps of the '393 patent. Thus, the process of the '393 patent is similar in function only to the second dehydrocyclodimerization reaction zone of this invention.

U.S. Pat. No. 4,686,312 to Chu et al discloses a multi-stage process for the production of aromatics from oxygen-containing hydrocarbons. The '312 process utilizes a feedstock different than the olefin-containing feedstock of this invention. U.S. Pat. No. 3,827,968 to Givens et al discloses a process for the production of aromatic hydrocarbons from a $C_5$⁻olefin-containing feedstock in a multi-stage process. The first stage of the '968 process is performed in the absence of hydrogen and is an oligomerization step while the second stage is an aromatization step. The '968 process differs in many respects from the instant process with the most notable differences being the function of the two reaction steps and the absence of hydrogen in the first oligomerization step.

European Patent application No. 0,162,636 describes a process for the production of aromatics from a light olefin-containing feedstock. The process comprises contacting the olefin-containing feedstock consecutively with two reaction zones containing the same catalyst where the first reaction zone catalyst has been deactivated by coke accumulation, and the second reaction zone catalyst is essentially fresh. The predominant reaction occurring in the first reaction zone is dehydrocyclodimerization of olefins while the predominant reaction in the second reaction zone is dehydrocyclodimerization of paraffins. The process of this invention differs from that described in European Patent application No. 0,162,636 in that essentially no desired liquid products are produced in the first reaction zone. The olefins are converted into paraffins in the instant process, not into aromatics as is accomplished in the prior art.

DESCRIPTION OF THE DRAWING

The single figure of this application is a process flow sheet depicting a typical conversion technique according to the present invention. The description will be directed towards the production of an aromatic hydrocarbon from a feed stream comprising $C_2$-$C_5$ olefins and paraffins. The description is not intended to limit the scope of the invention in anyway.

The first step of the process of the present invention comprises passing a mixed hydrocarbon feed stream 4 into a hydrogenation reaction zone 5 containing a hydrogenation catalyst, wherein the mixed feed stream 4 is comprised in part of a $C_2$-$C_5$ olefin and paraffinic hydrocarbon steam 1 and a hydrogen feed stream 3. The hydrogen feed stream is further characterized in that it may be supplied through line 14 as recovered hydrogen from the separation zone, it may be supplied as fresh hydrogen through line 2, or it may be a combination of both. Regardless of how the hydrogen is supplied to the hydrogenation reaction zone, the hydrogen is feed stream 3 combines with the $C_2$-$C_5$ olefinic and paraffinic hydrocarbon stream 1 along with the hydrogenation reaction zone effluent stream 7 to produce the mixed hydrocarbon feed stream 4 to the hydrogenation reaction zone 5.

The hydrogenation reaction zone effluent stream 6 is divided into two portions with the first portion comprising the hydrogenation reaction zone recycle stream 7 and the second portion comprising the fresh feed to the dehydrocyclodimerization reaction zone 10. The dehydrocyclodimerization reaction zone 10 accepts a combined feed through line 9 comprising a portion of the hydrogenation reaction zone effluent stream 8 along with recycled $C_2$-$C_5$ aliphatic hydrocarbons from the separation zone 12 through line 13.

The product of the dehydrocyclodimerization zone 10 passes into the separation zone 12 through line 11. The separation zone 12 comprises any means available for separating the aromatic-containing dehydrocyclodimerization effluent stream 11 into product fractions comprising hydrogen, methane, ethane, ethylene, $C_3$-$C_5$ aliphatic hydrocarbons, and $C_6$⁺aliphatic and aromatic hydrocarbons. The hydrogen is withdrawn from the separation zone 12 in line 15 where it may be divided into a net hydrogen stream 18 and into a recycle hydrogen stream 14 which is utilized as a portion to all of the hydrogenation reaction zone feedstock. The $C_6$⁺aliphatic and aromatic hydrocarbons are recovered from the separation zone 12 via line 17 while the methane and optionally a portion to all of the ethane and ethylene are recovered from the separation zone 12 via line 16. The dehydrocyclodimerization reaction zone recycle stream 13 comprises essentially all of the $C_3$-$C_5$ aliphatic hydrocarbons produced in the dehydrocyclodimerization reaction zone along with a portion of the ethane and ethylene produced as a result of the dehydrocyclodimerization reaction.

DETAILED DESCRIPTION

Processes for the conversion of light aliphatic hydrocarbons to aromatic or nonaromatic $C_6$⁺hydrocarbons have been the subject of significant development efforts as evidenced by the previously cited references. The basic utility of the process is the conversion of the low cost and highly available $C_2$-$C_5$ hydrocarbons into more valuable aromatic hydrocarbons and hydrogen or to convert the feed hydrocarbons to higher molecular weight aliphatic products. This may be desired simply to upgrade the value of the hydrocarbons. It may also be desired to correct an overabundance of $C_2$-$C_5$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals. The product aromatic hydrocarbons are also useful as blending components in high octane number motor fuels.

The feed compounds to this two-stage process are light aliphatic hydrocarbons having from 2 to 5 carbon atoms per molecule. The feed stream may comprise a single compound or a mixture of two or more of these compounds. The preferred feed compounds are propane, propylene, the butanes, and the butylenes, with saturates being highly preferred. The feed stream to the process may also contain various amounts of $C_2$ and $C_5$ hydrocarbons. It is preferred that the concentration of $C_5$ hydrocarbons in the feed stream to a dehydrocyclodimerization process is held to the minimum practical level, preferably below 5 mole percent.

It is an aspect of this invention that a portion to all of the $C_2$-$C_5$ aliphatic hydrocarbons fed to the process of this invention are olefinic hydrocarbons. It is preferred that the feedstock to this invention comprise at least 25 wt. % $C_2$-$C_5$ olefins since coking observed in a dehydrocyclodimerization reaction zone increases in relation to increasing olefin feed content. Therefore, feedstocks comprising very high amounts of olefins would be particularly deleterious to a dehydrocyclodimerization catalyst under normal conditions making this process more appealing.

The preferred products of the process are $C_6^+$ aromatic hydrocarbons. However, dehydrocyclodimerization processes are not 100% selective and some nonaromatic $C_6^+$ hydrocarbons are produced even from saturate feeds. When processing a feed made up of $C_2$-$C_5$ aliphatic hydrocarbons, the very great majority of the $C_6^+$ product hydrocarbons will be benzene, toluene, and the various xylene isomers. A small amount of $C_9^+$ aromatics is also produced. The presence of olefins in the feed stream typically would result in increased production of $C_6^+$ long chain aliphatic hydrocarbons. Sizable olefin concentrations in the feed also significantly decrease the production of aromatics. Both these problems and the coking problem discussed above are solved by the instant two-step process.

The subject invention is directed to increasing the amount of the more valuable $C_6^+$ alkylaromatics and also to increasing the catalyst life of a dehydrocyclodimerization catalyst by first hydrogenating the olefin-containing $C_2$-$C_5$ hydrocarbon feedstock followed by dehydrocyclodimerization of the hydrogenated feedstock.

The first step of the instant process is a hydrogenation reaction zone. The hydrogenation reaction zone contains a hydrogenation catalyst and operates at hydrogenation conditions sufficient to convert essentially all of the olefins in the $C_2$-$C_5$ aliphatic feedstock into paraffins such that the hydrogenated feedstock going to the second stage comprises essentially no olefins.

In a preferred embodiment, the feed to the first stage should be reasonably free of sulfur and other contaminants. If water-saturated, the feed need not be dry, but free water should be avoided. If the feed is not water-saturated, this dewatering step may be dispensed with.

Once water has been removed, the feed is typically combined with a small excess of hydrogen relative to the stoichiometric hydrogenation requirements. A recycle is maintained around the reactor to limit heat buildup in the reaction due to the exothermic process by limiting the maximum olefin concentration in the combined feed. Heat of reaction is removed by providing suitable cooling means on the recycle stream. The hydrogenation reaction proceeds over a fixed bed catalytic system at very mild conditions of pressure and temperature. Because of the very high activity of the catalyst, space velocities are high so that only relatively small reaction vessels and amounts of catalyst are required. In the absence of feed contaminants, the catalyst is very stable and its cost is economically insignificant.

The operating conditions at which the hydrogenation reaction is most efficient will vary depending upon the olefin makeup of the feed. It is conceivable that the hydrogenation step will occur at temperatures ranging from 50° to 250° C., at pressures ranging from 1.0 to 50.0 atmospheres and at a liquid hourly space velocity of 0.1 to 20.0 $hr^{-1}$. However, due to the exothermic nature of the process, it is most preferred that the hydrogenation reaction step occur at conditions including a temperature of from 50° to 150° C., a pressure of from 1.0 to 25 atmospheres, a liquid hourly space velocity of from 0.1 to 20.0 $hr^{-1}$, and with intermediate or final hydrogenated product recycle to the inlet of the reaction zone at a weight zone of recycle to fresh feed ranging from 1 to 20.

Hydrogen will be a co-feed to the hydrogenation reaction zone. The hydrogen feed rate is preferably slightly greater than the stoichiometric amount needed to saturate the feed olefins. However, the hydrogen rate can be much greater than stoichiometric without detrimentally affecting the hydrogenation reaction step. It is preferred that the hydrogen feed rate is 1 to 10 times stoichiometric requirements based upon the olefinic content of the hydrocarbon feed. This corresponds to a hydrogen-to-olefin molar feed ratio of 1:1 to 10:1.

Larger amounts of feed hydrogen are avoided to avoid the use of an intermediate product separation zone between the hydrogenation reaction zone. However, the use of an intermediate product separation zone is within the scope of this invention. The intermediate product separation zone, if used, will comprise any known means for separating hydrogen from hydrocarbons. Such a means might be a membrane separation zone or more preferably a vapor-liquid flash separation zone. Regardless of the means used, the intermediate separation zone would produce a vapor product comprising hydrogen which could be recycled to the hydrogenation reaction step or recovered as a product and a liquid product to the dehydrocyclodimerization reaction step.

The hydrogenation reaction step is further characterized in that at least 50 mole percent of the olefins in the hydrocarbon feed are hydrogenated into paraffins. Preferably, however, the hydrogenation of olefins in the hydrogenation reaction step is essentially complete. That is to say that after the hydrogenation step, the hydrocarbon feed contains essentially no olefins. By "essentially no olefins", it is meant that the hydrogenation hydrocarbons contain less than 2.0 wt. % olefins and preferably less than 0.5 wt. % olefins.

The catalyst that is useful in the instant hydrogenation process is one that is able to completely hydrogenate the olefins in the olefin-containing feed into a hydrogenation product that is essentially free of olefins as defined above. Any such catalyst of the prior art which has known hydrogenation properties and is able to produce an essentially olefin-free hydrogenation product will suffice. A particularly useful catalyst comprises a Group VII noble metal component, specifically palladium, on an inorganic oxide carrier.

The inorganic oxide carrier material useful as a catalyst of this process may be any carrier material known which is useful as a catalytic support. However, alumina is the most preferred support material. The most preferred inorganic oxide support of the present invention is alumina having a surface area of from 1 to 500 $m^2/g$. The alumina carrier material may be prepared in any suitable manner from synthetic or naturally occurring raw materials. The carrier may be formed in any desired shape such as spheres, pills cakes, extrudates, powders, granules, etc., and it may be utilized in any particle size. A preferred shape of alumina is the sphere. A preferred particle size is about 1/16-inch in diameter, though particles as small as about 1/32-inch and smaller may also be utilized as well as particles than 1/16-inch diameter.

In a most preferred method, the alumina is in the form of spheres. To make alumina spheres, aluminum metal is converted into an alumina sol by reacting it with a suitable peptizing acid and water, and then dropping a mixture of the sol and a gelling agent into a hot oil bath. The mixture forms spherical particles of an alumina gel in the hot oil bath which are easily converted into the preferred gamma- or eta-alumina carrier material by known methods including aging, drying, and calcining. Other shapes of the alumina carrier material may also be prepared by conventional methods.

As indicated above, one feature of the catalytic composite useful in the hydrogenation step of the process of this invention is a noble metal composition from Group VIII of the Periodic Table of the Elements. The Group VIII noble metal may be selected from the group consisting of platinum, palladium, iridium, rhodium, osmium, ruthenium, or mixtures thereof. Platinum or palladium are however the preferred Group VIII noble metal components, with palladium being most preferred. It is believed that substantially all of the Group VIII noble metal components exist within the catalyst in the elemental metallic state.

The Group VIII noble metal component generally will comprise about 0.01 to 10 wt. % calculated on an elemental basis, of the final catalyst composite Preferably, the catalyst comprises about 0.1 to 5 wt. % Group VIII noble metal component, especially about 0.1 to about 1.0 wt. % palladium.

The Group VIII noble metal component may be incorporated in the hydrogenation catalyst in any suitable manner such as, for example, by coprecipitation or cogelation, ion exchange or impregnation, or deposition from a vapor phase or from an atomic source or by like procedures either before, while, or after other catalytic components are incorporated. The preferred method of incorporating the Group VIII noble metal component is to impregnate the refractory oxide support with a solution or suspension of a decomposable compound of a Group VIII noble metal. For example, platinum may be added to the support by commingling the latter with an aqueous solution of chloroplatinic acid. Another acid for example, nitric acid or other optional components may be added to the impregnating solution to further assist in dispersing or fixing the Group VIII noble metal component in the final catalyst composite. The Group VIII noble metal component may be located upon the catalyst in a variety of useful manners known in the art including uniformly dispersed, surfaceimpregnated, or surface-concentrated, among others.

It is anticipated that the $C_2$-$C_5$ aliphatic hydrocarbon feed stream utilized in the process of the instant invention may originate as a product or byproduct of a refinery or petrochemical process. The light aliphatic hydrocarbons produced and recovered in a cracking or a reforming process would be examples of such process-derived feed streams. The products of a synthesis gas production process is another potential source of feed for the process described herein as is the light aliphatic hydrocarbons recovered at the wellhead at oil product facilities.

According to the process of the present invention, the feed stream is contacted with the hydrogenation catalyst in a hydrogenation reaction zone maintained at hydrogenation conditions. This contacting may be accomplished by using the catalytic composite in a fixed bed system, a moving bed system, a fluidized bed system, or in a bath-type operation; however, in view of the fact that attrition losses of the valuable catalyst should be minimized and of the wellknown operational advantages, it is preferred to use either a fixed bed catalytic system or a dense phase moving bed system such as is shown in U.S. Pat. No. 3,725,249. It is contemplated that in the case where a fixed bed catalytic system is employed to accomplish the process of the present invention, the catalyst of this invention may be contained in one or more fixed bed reactors, with the use of two or more reactors being preferred.

In a fixed bed system or in a dense-phase moving bed system, comprising two distinct reaction zones, the feed stream temperature is controlled by any suitable means and then passed into the first hydrogenation zone containing a bed of the instant catalytic composite. It is, of course, understood that the hydrogenation zone is preferably two separate reactors with suitable means therebetween to assure that the desired conversion temperature is maintained at the entrance of the first reactor. It is also important to note that the reactants may be contacted with the catalyst bed in either upward, downward, or radial flow fashion, with the latter being preferred. In addition, the reactants may be in the liquid phase, admixed liquid-vapor phase, or a vapor phase when they contact the catalyst, with the best results obtained in the vapor phase.

In a preferred two fixed bed reactor hydrogenation reaction system, the temperature of the first reaction zone is controlled by recycling a hydrocarbon slip stream withdrawn from the hydrogenation step between the first and second reactor. A cooling means is also preferably used on the recycle slip stream to remove heat therefrom generated by the exothermic hydrogenation reaction. As mentioned above, the weight ratio of the recycle slip stream to that of the fresh feed entering the hydrogenation step ranges from 1.0 to 20.

The essentially olefin-free liquid hydrogenation reaction step product is next passed into a dehydrocyclodimerization reaction step. The dehydrocyclodimerization step operates at dehydrocyclodimerization reaction conditions and contains a dehydrocyclodimerization reaction catalyst.

The feed compounds to the dehydrocyclodimerization reaction step are light paraffinic hydrocarbons from the hydrogenation step having from 2 to 5 carbon atoms per molecule. The feed stream may comprise a single compound or a mixture of two or more of these compounds. The preferred feed compounds are propane and butane. The preferred feed stream to the process may also contain some $C_2$ and $C_5$ hydrocarbons. It is preferred that the concentration of $C_5$ hydrocarbons in the feed stream to a dehydrocyclodimerization process is held to the minimum practical level, preferably below 5 mole percent. The preferred products of the process are $C_6$+aromatic hydrocarbons. However, dehydrocyclodimerization processes are not 100% selective and some nonaromatic $C_6$+hydrocarbons are produced even from saturate feeds. When processing a feed made up of propane and/or butane, the very great majority of the $C_6^+$ product hydrocarbons will be benzene, toluene, and the various xylene isomers. A small amount of $C_9^+$ aromatics is also produced.

The configuration of the reaction zone and the composition of the catalyst employed within the reaction zone are not basic elements of the invention or limiting characteristics of the invention. Nevertheless, in order to provide a background to the subject process, it is felt useful to describe the preferred reactor system for use in the invention. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081; and 4,403,909. These patents also describe catalyst regeneration systems and various aspects of moving catalyst bed operations and equipment. This reactor system has been widely employed commercially for the reforming of naphtha fractions. Its use has also been described for the dehydrogenation of light paraffins.

The preferred moving bed reactor system employes a spherical catalyst having a diameter between about 1/64-inch (0.04 cm) and ⅛-inch (0.32 cm). The catalyst preferably comprises a support material and a metallic component deposited on the support material as through impregnation or coprecipitation. The previously cited references point out that the current trend is the use of a zeolitic support material, with the catalyst referred to in the art as a ZSM-5 type zeolite often being specified as a preferred material. When properly formulated, it appears this zeolitic material by itself has significant activity for the dehydrocyclodimerization reaction. It is preferred to employ a metallic component within the catalyst system to increase the activity of the catalyst. The preferred metallic component is gallium.

The dehydrocyclodimerization conditions which will be employed for use with the process of the present invention will, of course, vary depending on such factors as feedstock composition and desired conversion. A desired range of conditions for the dehydrocyclodimerization of a feedstock comprising essentially all $C_2$-$C_5$ paraffinic hydrocarbons include a temperature from about 350° to about 700° C., a pressure from about 0.25 to about 20 atmospheres, and a liquid hourly space velocity from about 0.5 to about 20 hr$^{-1}$. The preferred process conditions are a temperature in the range from about 400° to 650° C., a pressure in the range of from 0.25 to 10 atmospheres, and a liquid hourly space velocity of between 0.5 and 10.0 hr$^{-1}$. It is understood that, as the average carbon number of the feed increases, a temperature in the lower end of temperature range is required for optimum performance and, conversely, as the average carbon number of the feed decreases, the higher the required temperature in the reaction zone.

The feed stream to the dehydrocyclodimerization process is defined herein as all streams introduced into the dehydrocyclodimerization reaction zone. Included in the feed stream is the $C_2$-$C_5$ paraffinic hydrocarbon. By "$C_2$-$C_5$ paraffinic hydrocarbon" is meant one or more open, straight, or branched chain isomers having from about 2 to 5 carbon atoms per molecule. Furthermore, the hydrocarbon in the feedstock is essentially saturated. That is, it comprises less than 2.0 wt. % olefins. Preferably, the hydrocarbons, $C_3$ and/or $C_4$, are selected from isobutane, normal butane and propane. Diluents may also be included in the feed stream. Examples of such diluents include hydrogen, nitrogen, helium, argon, neon, CO, $CO_2$, $NH_4$, $H_2O$ or its precursors. Water precursors are defined as those compounds which liberate $H_2O$ when heated to dehydrocyclodimerization reaction temperatures.

In addition to the hydrogenation reaction zone product stream, it is anticipated that a recycle stream comprising $C_2$-$C_5$ aliphatic hydrocarbons will be fed to the dehydrocyclodimerization reaction zone. The $C_2$-$C_5$ aliphatic hydrocarbon recycle stream will be recovered from the dehydrocyclodimerization reaction zone product stream for further processing. The recycle stream will preferably comprise $C_3$-$C_5$ aliphatic hydrocarbons along with a minor amount of ethane and ethylene. The recycle stream rate will vary depending upon the dehydrocyclodimerization reaction zone selectivity and conversion.

According to the present invention, the dehydrocyclodimerization reaction zone feed and recycle streams are contacted with a catalytic composite in a dehydrocyclodimerization reaction zone maintained at dehydrocyclodimerization conditions. This contacting may be accomplished by using the catalytic composite in a fixed bed system, a moving bed system, a fluidized bed system, or in a bath-type operation; however, in view of the danger of attrition losses of the valuable catalyst and of the well-known operation advantages, it is preferred to use either a fixed bed system or a dense-phase moving bed system such as shown in U.S. Pat. No. 3,725,249. It is contemplated that the contacting step can be performed in the presence of a physical mixture of particles of any dehydrocyclodimerization or similarly behaving catalyst of the prior art.

In a fixed bed system or a dense phase moving bed, the feed stream is preheated by any suitable heating means to the desired reaction temperature and then passed into a dehydrocyclodimerization zone containing a bed of the desired catalytic composite. It is, of course, understood that the dehydrocyclodimerization zone may be one or more separate reactors with suitable means therebetween to assure that the desired conversion temperature is maintained at the entrance to each reactor. It is also important to note that the reactants may be contacted with the catalyst bed in either upward, downward, or radial flow fashion, with the latter being preferred. In addition, the reactants may be in the liquid phase, admixed liquid-vapor phase, or a vapor phase when they contact the catalyst, with the best results obtained in the vapor phase. The dehydrocyclodimerization system then preferably comprises a dehydrocyclodimerization zone containing one or more fixed or dense phase moving beds of the instant catalytic composite. In a multiple bed system, it is, of course, within the scope of the present invention to use one dehydrocyclodimerization catalyst composite in less than all of the beds with another dehydrocyclodimerization or similarly behaving catalyst being used in the remainder of the beds. In a multiple reactor dehydrocyclodimerization zone, there may be one or more separate reactors with suitable heating means therebetween to compensate for any heat loss encountered in each catalyst bed. Specific to the dense phase moving bed system, it is common practice to remove catalyst from the bottom of the reaction zone, regenerate it by conventional means known to the art, and then return it to the top of the reaction zone.

The preferred catalyst useful in the dehydrocyclodimerization reaction step of the instant process comprises a phosphorus-containing alumina, a gallium component, and a crystalline aluminosilicate zeolite having a silica-to-alumina ratio of at least 12. The preferred catalyst is further characterized in that the crystalline aluminosilicate is ZSM-5 and is present in an amount ranging from 35 to 59.9 wt. %. In addition, the most preferred catalyst comprises from 0.1 to 5.0 wt. % gallium and from 40 to 60 wt. % of a phosphorus-containing alumina component. Such a catalyst is described in U.S. Pat. No. 4,636,483 which is incorporated herein by reference.

The hydrocarbon product of the two-step process of this invention is directed to a separation zone for separation into specific product fractions. The hydrocarbon product of the two-step process can be separated into fractions comprising hydrogen, methane, ethane and ethylene, $C_3$–$C_5$ aliphatic hydrocarbons, and $C_6^+$ aliphatic and aromatic hydrocarbons. The recovered hydrogen may be recycled in part as the hydrogen feed to the hydrogenation reaction step and/or recovered in part or total for use in hydrogen-consuming refinery processes such as a hydrocracking or hydrotreating processes. The $C_6^+$ aliphatic and aromatic hydrocarbons are recovered as the desired product of the two-step process. $C_3$–$C_5$ aliphatic hydrocarbons are recovered as feed recycle to the dehydrocyclodimerization reaction zone as described above. Finally, the ethane and ethylene are together typically divided with a portion of the ethane/ethylene product stream being combined with the $C_3$–$C_5$ aliphatic recycle stream to the dehydrocyclodimerization reaction step. The other ethane/ethylene portion is typically combined with the refractory methane stream and recovered as a light by-product stream. It is preferred that the dehydrocyclodimerization reaction zone combined feed comprise from 5.0 to 15.0 mole percent ethane.

The dehydrocyclodimerization reaction step product stream may be sent to any type of separation scheme known in the prior art capable of separating and recovering the product and recycle streams described above. U.S. Pat. No. 4,642,402 for example discloses a method of combining a reaction zone and product recovery zone to optimize the xylene produced in a dehydrocyclodimerization reaction. Additionally, it is anticipated that the product produced in the second reaction step of the process described herein may be recovered utilizing any method disclosed in the prior art. For instance, U.S. Pat. Nos. 3,537,978 and 3,574,089 describe the recovery of naphtha, hydrogen-rich recycle gas, and light hydrocarbon streams from the effluent of a catalytic reforming zone. U.S. Pat. No. 3,101,261 illustrates a process to recover light ends and naphtha from the effluent of a reforming reaction zone. These references are pertinent for their teaching the use of such separatory techniques as partial condensation, stripping columns, and absorption.

Processing schemes disclosed in the prior art as methods of improving process or separation efficacy are also anticipated as being useful as a portion of the process of the present invention. For example, U.S. Pat. Nos. 4,381,417 and 4,381,418 describe product recovery systems for dehydrogenation processes in which expansion of a gas stream provides fluids useful as coolant media. Referring to the latter reference, the reactor effluent is cooled, dried, further cooled, and then passed into a vapor-liquid separation zone 28. The vapors from this zone are depressurized in turbine 32 to yield a cold mixed phase stream collected in separation zone 34. Liquid from this zone is flashed into the separation zone 51.

U.S. Pat. No. 3,838,553 is pertinent for its description of the use of low temperatures and elevated pressures to affect the separation of vapors and for the integration of a low temperature separation zone with a standard vapor liquid type of separation zone. In FIG. 2 of this reference, the still high pressure effluent of the low temperature separation zone flows into a pressure swing adsorption zone.

Selectively permeable membranes are described in U.S. Pat. Nos. 4,180,388, 4,264,338, and 4,548,619. These references are also pertinent for their showing of various arrangements of two or more membrane separation units in various series flow with recycle and interstage compression.

The drawing illustrates the preferred embodiment of the invention. Those skilled in the art will recognize that this process flow diagram has been simplified by the elimination of many pieces of process equipment including some heat exchangers, process control systems, pumps, fractionation column overhead and reboiler systems, etc. which are not necessary to an understanding of the process. It may also be readily discerned that the process flow presented in the drawing may be modified in many aspects without departing from the basic overall concept of the invention. For example, the depiction of required heat exchangers in the drawing have been eliminated for purposes of simplicity. Those skilled in the art will recognize that the choice of heat exchange methods employed to obtain the necessary heating and cooling of various points within the process is subject to a large amount of variation as to how it is performed. In a process as complex as this, there exists many possibilities for indirect heat exchange between different process streams. Depending on the specific location and circumstance of the installation of the subject process, it may also be desired to employ heat exchange against steam, hot oil, or process streams from other processing units not shown on the drawing.

The following example will serve to illustrate a certain specific embodiment of the herein disclosed invention. This example should not, however, be construed as limiting the scope of the invention as set forth in the claims as there are many variations which may be made thereon without departing from the spirit of the invention, as those of skill in the art will recognize.

EXAMPLE

The following example is based upon pilot plant data obtained from both a complete olefin hydrogenation process and a dehydrocyclodimerization process.

An olefinic hydrocarbon feedstock is fed into a two-reactor hydrogenation reaction zone. The hydrogenation reaction zone was operated at a reactor inlet temperature of 149° C., an inlet absolute pressure of 21.7 atmospheres, and a liquid hourly space velocity of about 3.5 $hr^{-1}$. The catalyst is divided among the two reactors such that the first reactor contains 90% of the total catalyst volume and the second reactor contains 10% of the total catalyst volume. A recycle stream is passed from the outlet of the first hydrogenation reactor to the inlet of the same reactor at a rate of 8.9 moles of recycle hydrocarbons to 1 mole of fresh feed hydrocarbons. The hydrogenation catalyst comprises 0.5 wt. % palladium on an alumina base. The stream rates and compositions for the first hydrogenation reaction zone of the process can be found below in Table 1.

TABLE 1

| Hydrogenation Reaction Zone Stream Rates (kg/hr) | | | |
|---|---|---|---|
| Component | (HCBN Feed) | ($H_2$ Feed) | (Product) |
| $H_2$ | 0 | 259.3 | 7.5527 |
| $C_3$ | 3024.02 | 0 | 3024.02 |
| $IC_4$ | 4844.68 | 0 | 5643.32 |
| $=IC_4$ | 771.105 | 0 | 0.164415 |
| $=N_1C_4$ | 589.668 | 0 | 0.164415 |
| 13BD | 2721.55 | 0 | 0.00158507 |
| $NC_4$ | 0 | 0 | 0.164415 |
| Total (kg/hr) | 15818.6 | 259.3 | 16077.9 |

From Table 1, it can be seen that hydrogen is fed to the hydrogenation reaction zone at a rate such that slightly more than the stoichiometric amount required for olefin hydrogenation is supplied to the reaction zone. Additionally, it is evident that essentially all of the olefin hydrocarbons are hydrogenated into paraffinic hydrocarbons.

The hydrogenation reaction zone effluent stream (product) is then directed to the dehydrocyclodimerization reaction zone for conversion into aromatic hydrocarbons. The dehydrocyclodimerization reaction zone operates at an average reaction temperature of 540° C., a pressure of 5.1 atmospheres, and at a combined feed liquid hourly space velocity of about 2.35 $hr^{-1}$. The feedstock is contacted with a catalyst comprising approximately 50 wt. % of a crystalline aluminosilicate zeolite, 49.0 wt. % of a phosphorus-containing alumina component having a phosphorus content of about 22 wt. %, and about 1 wt. % of a gallium component. The method of making such a catalyst is disclosed in U.S. Pat. No. 4,636,483. The results of the dehydrocyclodimerization process step can be found below in Table 2.

TABLE 2

| Dehydrocyclodimerization Reaction Zone Stream Rates (kg/hr) | | |
|---|---|---|
| Component | Hydrocarbon Feed | Hydrocarbon Product |
| $H_2$ | 7.6 | 618.3 |
| $C_1$ | — | 3158.0 |
| $C_2$ | — | 2481.3 |
| $=C_2$ | — | 92.7 |
| $C_3$ | 3024.0 | 376.7 |
| $=C_3$ | — | 24.2 |
| $nC_4$ | 7402.6 | 65.7 |
| $iC_4$ | 5643.3 | |
| $=C_4$'s | Trace | 3.6 |
| $C_5$ | — | 4.6 |
| $C_6$ Aliphatics | — | 0 |
| $C_6^+$ Aromatics | — | 8836.2 |
| Naphthalenes | — | 409.6 |
| Total (kg/hr) | 16077.5 | 16071.0 |

It is evident from the data in Table 2 above that a paraffinic hydrocarbon feedstock is readily converted into an aromatic-containing product in the second reaction stage of the instant process.

What is claimed is:

1. A continuous multi-stage catalyst process for producing aromatic hydrocarbons from a feedstock comprising $C_2$-$C_5$ olefins by the steps of:
    (a) passing the $C_2$-$C_5$ hydrocarbon feedstock comprising olefins along with hydrogen into a hydrogenation reaction zone containing a hydrogenation catalyst and operated at hydrogenation reaction conditions to produce a hydrogenation reaction zone product containing at least 50 mole percent fewer olefinic hydrocarbons than the $C_2$-$C_5$ hydrocarbon feedstock;
    (b) passing the hydrogenation reaction zone product into a dehydrocyclodimerization reaction zone containing a dehydrocyclodimerization catalyst and operated at dehydrocyclodimerization reaction conditions to produce a dehydrocyclodimerization reaction zone product comprising hydrogen, methane, ethane, ethylene, $C_3$-$C_5$ aliphatic hydrocarbons, $C_6^+$ aliphatic hydrocarbons, and aromatic hydrocarbons; and
    (c) recovering the products of the dehydrocyclodimerization reaction zone.

2. The process of claim 1 further characterized in that the dehydrocyclodimerization product fractions comprising a portion to all of the ethane and ethylene and a portion to all of the $C_3$-$C_5$ aliphatic hydrocarbons is recycled to the inlet of the dehydrocyclodimerization reaction zone.

3. The process of claim 1 further characterized in that the hydrogenation reaction zone product stream passes into a vapor-liquid separation zone before passing into the dehydrocyclodimerization reaction zone for the purpose of removing hydrogen from the hydrogenation reaction zone process stream.

4. The process of claim 1 further characterized in that the hydrogenation reaction zone process conditions include a temperature of from 50° to 250° C., a pressure of from 1.0 to 50 atmospheres, and a liquid hourly space velocity of from 0.1 to 20 $hr^{-1}$.

5. The process of claim 1 further characterized in that the dehydrocyclodimerization reaction zone process conditions include a temperature of from 350° to 700° C., a pressure of from 0.25 to 20 atmospheres, and a liquid hourly space velocity of from 0.5 to 20 $hr^{-1}$.

6. A continuous multi-stage catalytic process for producing aromatic hydrocarbons from a feedstock comprising $C_2$-$C_5$ olefins by the steps of:
    (a) passing the $C_2$-$C_5$ hydrocarbon feedstock comprising olefins along with hydrogen into a hydrogenation reaction zone containing a hydrogenation catalyst and operated at hydrogenation conditions including a temperature of from 50° to 150° C., a pressure of from 1.0 to 25 atmospheres, and a liquid hourly space velocity of from 0.1 to 20.0 $hr^{-1}$ to produce a hydrogenation reaction zone product comprising essentially no olefins;
    (b) passing the hydrogenation reaction zone product comprising essentially no olefins along with a recycle stream comprising ethane, ethylene and $C_3$-$C_5$ aliphatic hydrocarbons recovered in step (c) into a dehydrocyclodimerization reacting zone containing a dehydrocyclodimerization catalyst and operated at dehydrocyclodimerization reaction conditions including a temperature of from 400° to 650° C., a pressure of from 0.25 to 10 atmospheres, and a liquid hourly space velocity of from 0.5 to 10 $hr^{-1}$ to produce a dehydrocyclodimerization reaction zone product comprising hydrogen, methane, ethane, ethylene, $C_3$-$C_5$ hydrocarbons, and $C_6^+$ aliphatic and aromatic hydrocarbons;
    (c) separating in a separation zone the dehydrocyclodimerization reaction zone product into at least four fractions comprising:
        (i) hydrogen;
        (ii) methane;
        (iii) ethane, ethylene and $C_3$-$C_5$ aliphatic hydrocarbons; and (iv) C$_6$+aliphatic and aromatic hydrocarbons; and (d) recycling fraction (iii) of step (c) to the dehydrocyclodimerization reaction zone as a portion of the dehydrocyclodimerization reaction zone feedstock and recovering the remaining fractions as products.

7. The process of claim 6 further characterized in that the hydrocarbon feedstock to the continuous multistage process comprises C$_3$ and C$_4$ olefins.

8. The process of claim 6 further characterized in that hydrogen is fed to the hydrogenation reaction zone at a hydrogen-to-olefin molar feed ratio of from 1:1 to 10:1.

9. The process of claim 6 further characterized in that the dehydrocyclodimerization reaction zone catalyst comprises a crystalline aluminosilicate zeolite component, a phosphorus-containing alumina component, and a component selected from the elements of Group IIB–IVB of the Periodic Table of the Elements.

10. The process of claim 6 further characterized in that a portion of the hydrogenation reaction zone product stream is recycled to the inlet of the hydrogenation reaction zone.

11. The process of claim 10 further characterized in that the weight ratio of the recycle hydrogenation reaction zone product to the weight of the fresh feed fed to the inlet of the hydrogenation reaction zone ranges from 1 to 20.

12. The process of claim 6 further characterized in that the hydrogenation reaction zone product stream passes into a vapor-liquid separation zone prior to passing into the dehydrocyclodimerization reaction zone for the purpose of removing hydrogen from the hydrogenation reaction zone product stream.

13. The process of claim 6 further characterized in that hydrogen recovered from the dehydrocyclodimerization reaction zone products is recycled as a portion to all of the hydrogen feed to the hydrogenation reaction zone.

* * * * *